United States Patent
Pible et al.

(10) Patent No.: US 6,952,259 B2
(45) Date of Patent: Oct. 4, 2005

(54) METHOD OF DETECTING THE PRESENCE OF A LIQUID IN A MIX

(75) Inventors: Olivier Pible, Avignon (FR); Emmanuel Bois, St Paul les Fonts (FR)

(73) Assignee: CIS BIO International, Saclay (FR)

(*) Notice: Subject to any disclaimer, the term of this patent is extended or adjusted under 35 U.S.C. 154(b) by 263 days.

(21) Appl. No.: 10/296,970

(22) PCT Filed: May 28, 2001

(86) PCT No.: PCT/IB01/00944
§ 371 (c)(1),
(2), (4) Date: May 16, 2003

(87) PCT Pub. No.: WO01/92882
PCT Pub. Date: Dec. 6, 2001

(65) Prior Publication Data
US 2004/0036869 A1 Feb. 26, 2004

(30) Foreign Application Priority Data
Jun. 2, 2000 (FR) .............................. 00 07108

(51) Int. Cl.⁷ ............................ G01J 3/30; G01N 21/64
(52) U.S. Cl. ................................... 356/318; 250/458.1
(58) Field of Search ................................. 356/317–318, 356/417; 250/458.1–461.2; 422/82.07–82.08; 436/172, 19

(56) References Cited

U.S. PATENT DOCUMENTS

| | | | |
|---|---|---|---|
| 3,612,866 A | * | 10/1971 | Stevens ...................... 436/172 |
| 4,476,095 A | | 10/1984 | Scott et al. |
| 4,794,085 A | | 12/1988 | Jessop et al. |
| 5,590,052 A | | 12/1996 | Kopf-Sill et al. |
| 2002/0177235 A1 | * | 11/2002 | Mabile et al. ............... 436/172 |

FOREIGN PATENT DOCUMENTS

| | | | |
|---|---|---|---|
| EP | 0 180 492 | 5/1986 | |
| EP | 0 355 849 A2 | * 8/1989 | .......... G01N/21/64 |
| EP | 0 355 849 | 2/1990 | |
| EP | 0 539 477 | 1/1992 | |
| EP | 0 321 353 | 5/1992 | |
| EP | 0 601 113 | 6/1994 | |
| FR | 2 769 315 | 4/1999 | |
| WO | WO 98/15830 | 4/1998 | |
| WO | WO 99/18114 | 4/1999 | |

* cited by examiner

Primary Examiner—Gregory J. Toatley, Jr.
Assistant Examiner—Kara Geisel
(74) Attorney, Agent, or Firm—Millen White Zelano & Braniga, P.C.

(57) ABSTRACT

The invention relates to a method of detecting the presence of a liquid introduced into a mix of constituents. The method comprises the following steps:

excitation of the mix by a light signal in the absence of the liquid to be detected;

measurement of a fluorescence signal over a time $\Delta t$ characteristic of the liquid to be detected, so as to produce a reference quantity Ro;

introduction of an amount of liquid to be detected in the mix;

excitation of the mix by a light signal;

measurement of a fluorescence signal over a time $\Delta t$ so as to produce a quantity R;

comparison of the quantity R with a quantity k×Ro.

The invention applies to the detection of serum pipetting errors within the context of bioassays, especially immunological tests.

20 Claims, 3 Drawing Sheets

METHOD OF DETECTING THE PRESENCE OF A LIQUID IN A MIX

The present invention relates to a method of detecting the presence of a liquid in a mix.

The invention will be more particularly described within the context of detecting the presence of a liquid, for example, serum, introduced into a mix as the result of a pipetting operation.

Pipetting a liquid is an operation consisting in filling a pipette with liquid by suction. Pipetting operations are encountered, for example, in laboratories for introducing various liquids into test cells usually called wells. The liquid introduced into the test cells must therefore by in a sufficient amount for the test results to be able to be validated. A pipetting error may cause serious problems. This is the case, in particular, when the liquid sucked up by pipetting is a serum intended for carrying out disease screening tests such as, for example, cancer screening tests.

Most automatic analysers do not include a pipetting error detection system. The only known devices are based on measurements carried out during the pipetting. These may be pressure measurements (measurement of the pressure difference between air pipetting and liquid pipetting) or measurements for monitoring a liquid detection signal during the pipetting.

U.S. Pat. No. 4,794,085 describes a device which uses pressure measurements to detect liquid pipetting errors. Such a device requires the use of specific pressure measurement means which are bulky and difficult to use. Moreover, only a break in the liquid during pipetting can be detected. Defective pipetting not due to a break is not detectable.

The invention does not have the abovementioned drawbacks.

Thus, the invention relates to a method of detecting the presence of a liquid in a mix, characterized in that it comprises the following steps:

production of a first mix not containing the liquid to be detected;

excitation of the first mix by a light signal of wavelength $\lambda$;

measurement of a fluorescence signal S1 emitted by the first mix over a time $\Delta t$ close to a lifetime $\tau 1$ characteristic of the liquid to be detected, so as to produce a reference quantity Ro which is a function of the measured signal S1;

production of the mix from constituents identical to the constituents making up the first mix and from an amount of the liquid to be detected;

excitation of the mix by a light signal of wavelength $\lambda$;

measurement of a fluorescence signal S11 emitted by the mix over the time $\Delta t$ close to the lifetime $\tau 1$ so as to produce a quantity R which is a function of the measured signal S11;

comparison of the quantity R with a quantity k×Ro.

The expression "time $\Delta t$ close to the lifetime $\tau 1$" should be understood to mean a time sufficiently close to the lifetime $\tau 1$ so that in the presence of liquid in the mix, the signal detected is an unambiguous indicator that this liquid is present.

According to a first way of implementing the invention, the mix is produced by introducing the amount of liquid to be detected into the first mix.

According to a second way of implementing the invention, the mix is produced by mixing the amount of liquid to be detected into a second mix substantially identical to the first mix.

The mix containing the liquid to be detected can be dispensed into N separate wells, N being an integer.

Advantageously, the steps of producing the first mix, of exciting the first mix, of measuring a fluorescence signal emitted by the first mix and of calculating the reference quantity Ro may be carried out only for M specimens, M being an integer greater than or equal to 1 and less than or equal to N, whereas the steps of exciting the mix, of measuring the fluorescence signal emitted by the mix, of calculating the quantity R and of comparing R with k×Ro are carried out for each of the N wells.

If an operation of pipetting the liquid to be detected intervenes in the production of the mix, the method according to the invention allows pipetting errors to be detected. The invention therefore also relates to a method of detecting an error in pipetting a liquid, characterized in that it employs a method of detecting the presence of liquid, such as the abovementioned method according to the invention.

Furthermore, the presence of the liquid may be established very accurately. It is not only possible to make a qualitative measurement (liquid present: yes or no), but also a quantitative measurement. Another advantage of the invention consists in being able to detect the liquid at any moment after introducing the liquid into the mix.

Further features and advantages of the invention will become apparent on reading the description of ways of implementing the invention, with reference to the appended figures in which.

In all the figures, the same reference numbers denote the same components.

By way of non-limiting example, in the rest of the description the liquid whose presence is to be detected is serum. However, the invention relates more generally to any type of liquid capable of being detected by the emission of time-resolved fluorescence.

Figure 1:
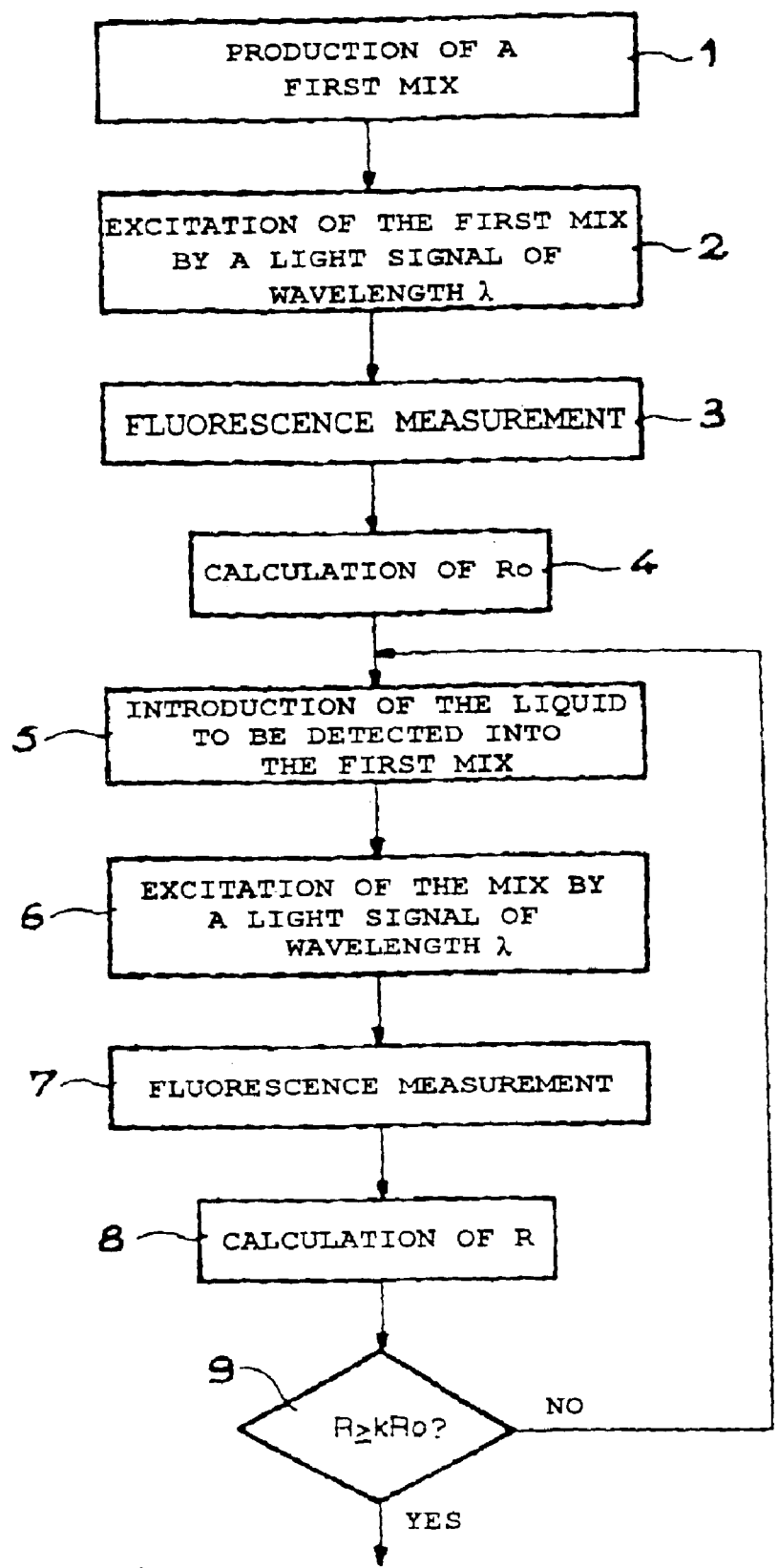
FIG. 1 shows a flowchart of a first way of implementing the detection method according to the invention.

FIG. 1 shows a flowchart of a first way of implementing the method of detecting the presence of a liquid according to the invention.

The method according to the first way of implementing the invention starts with a step 1 of producing a first mix. The first mix does not contain any serum. The first mix comprises at least one constituent Ci capable of emitting a fluorescence signal of wavelength $\lambda i$ due to the action of an excitation signal of wavelength $\lambda$.

A step 2 of exciting the first mix by a light signal of wavelength $\lambda$ follows step 1. Due to the action of the light signal of wavelength $\lambda$, a fluorescence signal is then emitted by the constituent(s) Ci of the mix.

Analysis of the time spectrum of the de-excitation caused by emission of a fluorescence signal by a mixture of constituents shows that the signal emitted as the result of a pulsed excitation is the sum of individual signals, each individual signal being characteristic of one constituent Ci of the mix. The fluorescence signal F can therefore be written as:

$$F = \Sigma(Ai \times \exp(-t/\tau i)),$$

where Ai and $\tau i$ are the amplitude and the lifetime, respectively, of an individual signal characteristic of the constituent Ci.

In the case of serum, for example, the fluorescence signal seen through a read system based on a photomultiplier used for counting photons, is characterized by a lifetime $\tau 1$ of the order of 5 $\mu s$.

A fluorescence measurement step 3 follows the excitation step 2. A fluorescence signal S1 is measured within a time slot Δt of duration close to the characteristic lifetime of the signal to be detected. If the liquid to be detected is serum, the time Δt is, for example, the time interval (5 μs, 20 μs) starting from the instant of excitation of the mix. The signal thus measured is used to calculate a reference quantity Ro in a calculation step 4.

According to a first variant of the method of the invention, the reference quantity Ro is equal to the measured signal S1. According to a second variant, a second fluorescence signal S2 is measured, during step 3, in a time slot ΔT outside the time Δt. The time slot ΔT may, for example, be the time interval (100 μs, 3000 μs) counting from the instant of excitation of the mix. The reference quantity Ro calculated in step 4 is then equal to the ratio of the signal S1 to the signal S2.

According to the second variant of the method of the invention, we can therefore write:

$$Ro=S1/S2.$$

The advantage of establishing a quantity Ro in the form of a ratio of the signals S1 and S2 will become apparent further on (cf. step 8).

Once the fluorescence has been measured, the serum is introduced into the first mix in a step 5. A new step 6 of exciting the mix by means of a signal of wavelength λ follows step 5 and a new fluorescence measurement (step 7) follows step 6. A fluorescence signal S11 is thus measured in a time slot Δt as mentioned above. The signal S11 is then used to calculate, in step 8, a quantity R which is a function of the amount of serum present in the mix.

According to the abovementioned first variant of the method of the invention, the quantity R is equal to the measured signal S11. According to the second variant, a second signal S22 is measured in step 7. The signal S22 is measured in a time slot ΔT as mentioned above. The quantity R calculated in step 8 is then equal to the ratio of the signal S11 to the signal S22. We may therefore write:

$$R=S11/S22.$$

The signal S11 is proportional to the amount of serum detected. The fact of dividing the signal S11 by the signal S22 advantageously allows the measurement S11 to be normalized, by taking into account the optical absorbence of the mix induced by the serum. The quantity R is then independent of the absorbence characteristics of the serum and represents only a relative level of the serum signal.

A comparison between the quantity R and a quantity equal to k×Ro is then made (step 9). If R is greater than or equal to k×Ro, then the amount of serum introduced into the mix in step 5 is regarded as sufficient. Otherwise, the amount introduced is regarded as insufficient and a new step of introducing serum must be carried out (return to step 5). Advantageously, the coefficient k may be chosen taking into account the statistical fluctuations of R in order, for example, to avoid any unjustified detection. If R and Ro are measured substantially at the same instant of an incubation cycle, the number k is a number greater than 1. If R and Ro are measured at substantially different instants of an incubation cycle the number k may be less than 1 because of the signal fluctuations during incubation.

In certain applications, the mixture of constituents to be tested is dispensed into N separate wells. Advantageously, steps 2, 3 and 4 may be carried out only on a few, or even only on one, of the N wells, whereas steps 5, 6, 7, 8 and 9 relate to all of the N wells.

Figure 2:
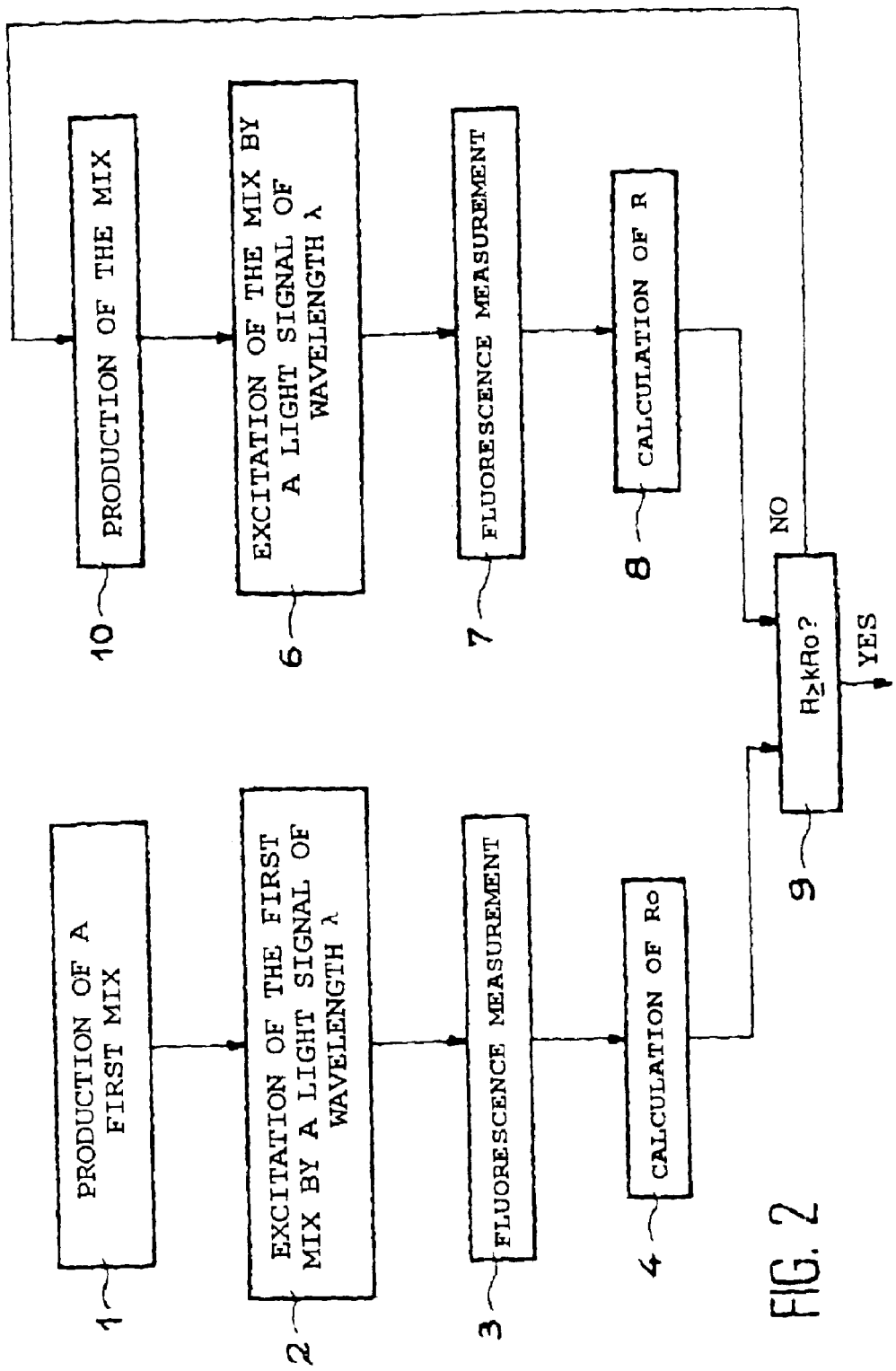
FIG. 2 shows a flowchart of a second way of implementing the detection method according to the invention.

FIG. 2 shows a flowchart of a second way of implementing the detection method according to the invention.

The second way of implementing the method of the invention also comprises the steps of producing a first mix (1), exciting the first mix (2), measuring a fluorescence signal emitted by the first mix (3) and calculating the reference quantity Ro (4) as described above.

According to the second way of implementing the invention, the mix containing the liquid to be detected is produced (in step 10), not by introducing the liquid to be detected into the first mix but by mixing the amount of liquid to be detected into a second mix substantially identical to the first mix. The expression "second mix substantially identical to the first mix" should be understood to mean a second mix containing the same constituents as the first mix in substantially identical amounts. The mix containing the liquid to be detected may be obtained by pipetting the various components of which it is composed.

Once the mix has been produced, the method according to the second way of implementing the invention comprises the successive steps of exciting the mix (step 6), of measuring the fluorescence (step 7) and of calculating the quantity R (step 8). The quantity R is then compared (step 9) with the quantity Ro. If R is greater than or equal to k×Ro then the amount of serum present in the mix produced in step 10 is regarded as sufficient. Otherwise, the amount of serum is regarded as insufficient and a new mix must be produced (return to step 10).

According to a variant of the second way of implementing the invention, the first mix also contains a liquid which does not exhibit fluorescence characteristics at the wavelength λ. This liquid, which is inert from the standpoint of fluorescence characteristics, then allows the first mix to have an overall volume substantially identical to the overall volume of the mix containing the liquid to be detected. It is therefore possible to ensure optimum setting of the measurement device.

In general, the invention finds particularly advantageous application if the constituents of the mix other than the liquid whose presence is to be detected must also be measured by time-resolved fluorescence.

The device used for taking the intended fluorescence measurements may therefore also be used to take measurements indicating whether the amount of liquid present in the mix is sufficient. Advantageously, no additional dedicated device for detecting the liquid is therefore necessary.

This is the case, for example, when carrying out bioassays, such as, for example, immunological tests using fluorescent labels. In the case of immunological tests using time-resolved fluorescence in a homogeneous phase, as described in the European Patent specification published under No. 0 539 477, the mixture of constituents comprises a donor conjugate and an acceptor conjugate. The donor conjugate may contain a biologically active molecule labelled by a buffered rare-earth chelate or cryptate and the acceptor conjugate may contain a biologically active molecule labelled by a buffered fluorescent acceptor compound. By way of non-limiting examples, the biologically active molecule may be chosen from an antibody, an antigen, a peptide, a protein, a receptor, a ligand, a nucleic acid, a nucleotide or a drug and the fluorescent acceptor compound may be chosen from fluorescent phycobiliproteins (allophycocyanine, allophycocyanine B, C-phycocyanine or R-phycocyanine) or fluorescent organic molecules.

The rare earth cryptates used for these bioassays are disclosed in European Patent specifications filed under the name CIS BIO International and published under the numbers EP 0 180 492, EP 0 321 353 and EP 0 601 113.

Figure 3:
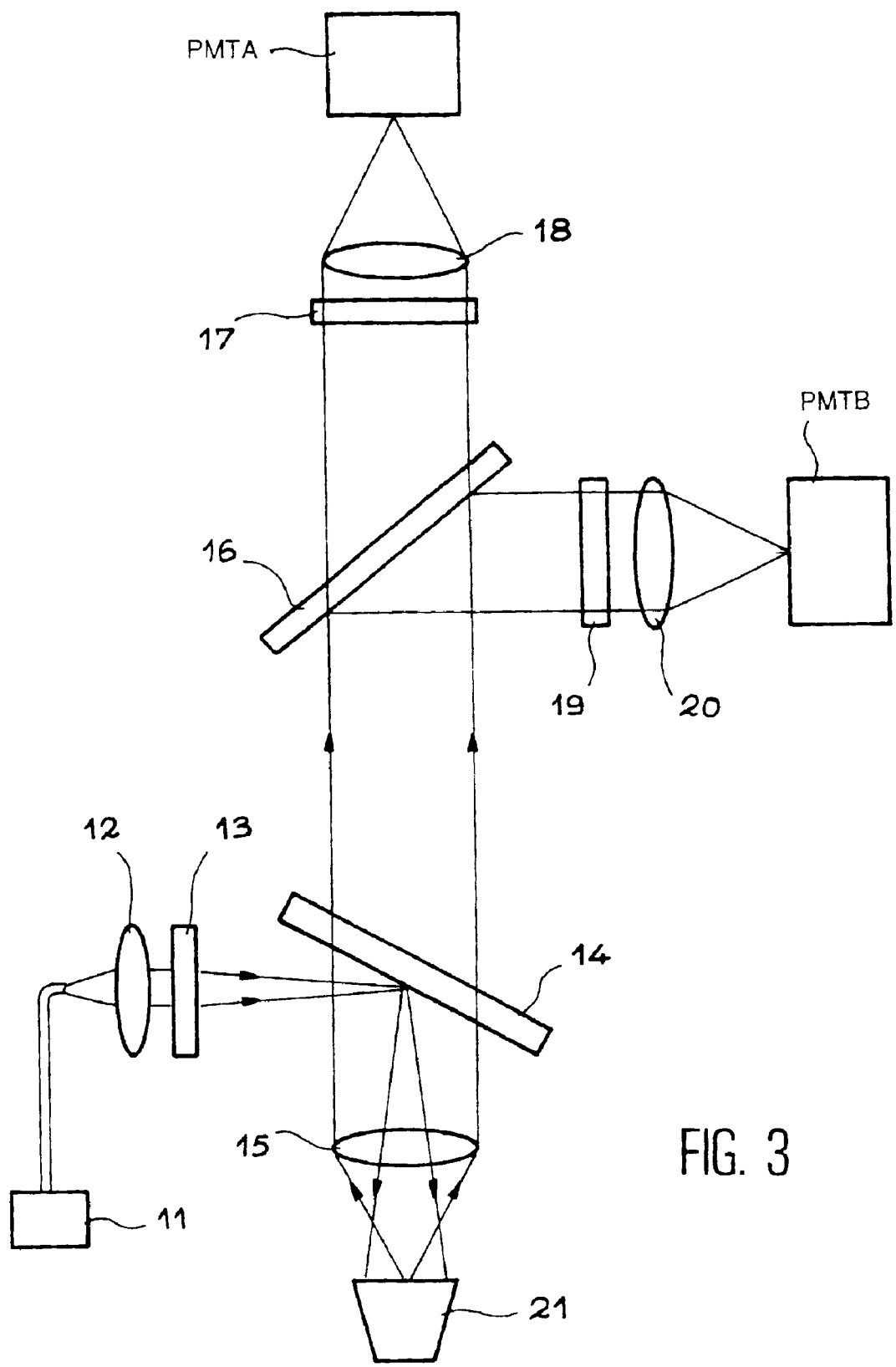
FIG. 3 shows one embodiment of a measurement device for implementing the detection method according to the invention.

The device described in FIG. 3 shows a fluorescence measurement device for carrying out bioassays, like those mentioned above. By way of example, the device described in FIG. 3 shows an embodiment of a time-resolved fluorescence measurement device for implementing the method according to the invention.

By way of non-limiting example in the rest of the description, the donor conjugate is a conjugate containing an antibody labelled with a buffered europium cryptate and the acceptor conjugate is a conjugate containing an antibody labelled with a fluorescent acceptor compound. The liquid introduced into the mix is serum.

The device in FIG. 3 comprises a nitrogen laser source 11 emitting light of 337 nm wavelength, a focussing lens 12 associated with a band-pass filter 13 centred around 337 nm, a dichroic mirror 14, a collector objective 15, a dichroic beam splitter 16, a band-pass filter 17 centred around 665 nm associated with a focussing lens 18, a band-pass filter 19 centred around 620 nm associated with a focussing lens 20, a photomultiplier PMTA for detecting photons of 665 nm wavelength, a photomultiplier PMTB for detecting photons of 620 nm wavelength and a test cell 21 containing the mix to be studied (acceptor conjugate, donor conjugate and serum).

The dichroic mirror 14 makes it possible for the light emitted by the laser source 11, after being focussed (12) and filtered (13) to be directed onto the test cell (21). The constituents of the mix are then excited by the light that they receive. A working fluorescence signal at the 665 nm wavelength emitted by the acceptor is measured by the photomultiplier PMTA. At the same time, a fluoresence signal at the 620 nm wavelength emitted by the europium cryptate is measured by the photomultiplier PMTB. The signal emitted by the europium cryptate is used as reference signal. The result of the measurement is in the form of the ratio of the working signal emitted by the acceptor to the reference signal emitted by europium cryptate. Absorption of the excitation energy or of the emission energy is therefore able to give a weaker signal without the ratio being modified.

Within the context of implementing the method according to the invention using a device as described in FIG. 3, the excitation signal of wavelength $\lambda$ is a signal of 337 nm wavelength emitted by the laser source 11, the signals S1 and S11, measured over the time $\Delta t$ close to the lifetime $\tau 1$ characteristic of the serum, are signals whose wavelength is equal to either 620 nm or 665 nm and the signals S2 and S22, measured over the time $\Delta T$ outside the time $\Delta t$, are signals whose wavelength is equal to either 620 nm or 665 nm.

As mentioned above, the fluorescence measurement device of FIG. 3 applies to a broad range of donor and acceptor conjugates. The laser source 11 may therefore be a light source whose wavelength varies between 300 nm and 400 nm approximately. Likewise, the fluoresence signal emitted by the donor conjugate may have a wavelength $\lambda 1$ which varies between 500 nm and 750 nm approximately and the fluorescence signal emitted by the acceptor conjugate may have a wavelength $\lambda 2$ which varies between 550 nm and 850 nm approximately.

The method according to the invention therefore also relates to an implementation in which the wavelength $\lambda$ of the excitation signal lies, for example, approximately between 300 nm and 400 nm and wavelengths of the fluorescence signals S1, S2, S11 and S22 lie, for example, within the [500 nm–750 nm] range or within the [550 nm–850 nm] range.

What is claimed is:

1. A method of detecting the presence of a liquid in a mix, comprising:
producing a first mix not containing the liquid to be detected;
exciting the first mix by a light signal of wavelength $\lambda$;
measuring a fluorescence signal S1 emitted by the first mix over a time $\Delta t$ close to a lifetime $\tau 1$ characteristic of the liquid to be detected, so as to produce a reference quantity Ro which is a function of the measured signal S1;
producing the mix from constituents identical to the constituents making up the first mix and from an amount of the liquid to be detected;
exciting the mix by a light signal of wavelength $\lambda$;
measuring a fluorescence signal S11 emitted by the mix over the time $\Delta t$ close to the lifetime $\tau 1$ so as to produce a quantity R which is a function of the measured signal S11; and
comparing the quantity R with a quantity k×Ro, wherein k is a coefficient that takes into account the statistical fluctuations of R.

2. A method according to claim 1, wherein the mix is produced by introducing the amount of liquid to be detected into the first mix.

3. A method according to claim 2, wherein the amount of liquid to be detected is introduced by pipetting.

4. A method according to claim 1, wherein the mix is produced by mixing the amount of liquid to be detected into a second mix substantially identical to the first mix.

5. A method according to claim 4, wherein the first mix contains a liquid which does not have fluorescence characteristics at the wavelength $\lambda$ so that the overall volume of the first mix is substantially identical to the overall volume of the mix.

6. A method according to claim 4, wherein the first mix and the mix containing the liquid to be detected are each obtained by pipetting their respective components.

7. A method according to claim 1, wherein the first mix comprises at least one constituent Ci capable of emitting a fluoresence signal of wavelength $\lambda i$ due to the action of an excitation signal of wavelength $\lambda$.

8. A method according to claim 1, wherein the quantities Ro and R are equal to the measured signals S1 and S11, respectively.

9. A method according to claim 8, wherein the first mix comprises at least two constituents C1 and C2 associated with the respective wavelengths $\lambda 1$ and $\lambda 2$ and in that the fluorescence signals S1 and S11 are signals whose wavelength is equal to either $\lambda 1$ or $\lambda 2$.

10. A method according to claim 1, wherein the quantity Ro is equal to the ratio of the measured fluorescence signal S1 to a fluorescence signal S2 measured over an integration time $\Delta T$ outside the time $\Delta t$ and in that the quantity R is equal to the ratio of the measured fluorescence signal S11 to a fluorescence signal S22 measured over the integration time $\Delta T$.

11. A method according to claim 10, wherein the first mix comprises at least two constituents C1 and C2 associated with the respective wavelengths $\lambda 1$ and $\lambda 2$ and in that the fluorescence signals S1, S2, S11 and S22 are signals whose wavelength is equal to either $\lambda 1$ or $\lambda 2$.

12. A method according to claim 7, wherein a first constituent C1 is a conjugate containing a biologically active molecule labelled by a buffered rare-earth chelate or cryptate and a second constituent C2 is a conjugate containing a biologically active molecule labelled by a buffered fluorescent acceptor compound, the wavelength λ lying approximately between 300 nm and 400 nm, the wavelength λ1 lying approximately between 500 nm and 750 nm and the wavelength λ2 lying approximately between 550 nm and 850 nm.

13. A method according to claim 12, wherein the biologically active molecules are chosen from antibodies, antigens, peptides, proteins, receptors, ligands, nucleic acids, nucleotides and drugs and in that the fluorescent acceptor compound is a phycobiliprotein, or a fluorescent organic molecule.

14. A method according to claim 1, wherein the liquid to be detected is serum.

15. A method according to claim 1, wherein producing the first mix, of exciting the first mix and of measuring a fluorescence signal emitted by the first mix are carried out on M samples, M being an integer greater than or equal to 1, the mix is produced in N separate wells, N being an integer greater than or equal to M, and exciting the mix and of measuring a fluorescence signal emitted by the mix are being carried out for each of the N wells.

16. A method of detecting errors in the pipetting of a liquid, comprising a method according to claim 3.

17. A method according to claim 12, wherein the fluorescent acceptor compound is a phycobiliprotein of an allophycocyanine, an allophycocyanine B, a C-phycocyanine, or an R-phycocyanine.

18. A method of detecting the presence of a liquid in a mix, comprising steps for:

production (1) of a first mix not containing the liquid to be detected;

excitation (2) of the first mix by a light signal of wavelength λ;

measurement (3) of a fluorescence signal S1 emitted by the first mix over a time At close to a lifetime τcharacteristic of the liquid to be detected, so as to produce (4) a reference quantity Ro which is a function of the measured signal S1;

production (5, 10) of the mix from constituents identical to the constituents making up the first mix and from an amount of the liquid to be detected;

excitation (6) of the mix by a light signal of wavelength λ;

measurement (7) of a fluorescence signal S11 emitted by the mix over the time Δt close to the lifetime ri so as to produce (8) a quantity R which is a function of the measured signal S11; and comparison (9) of the quantity R with a quantity k×Ro, wherein k is a coefficient that takes into account the statistical fluctuations of R.

19. A method according to claim 18, wherein the mix is produced by introducing the amount of liquid to be detected into the first mix.

20. A method according to claim 18, wherein the mix is produced by mixing the amount of liquid to be detected into a second mix substantially identical to the first mix.

* * * * *

UNITED STATES PATENT AND TRADEMARK OFFICE
CERTIFICATE OF CORRECTION

PATENT NO. : 6,952,259 B2
DATED : October 4, 2005
INVENTOR(S) : Pible et al.

It is certified that error appears in the above-identified patent and that said Letters Patent is hereby corrected as shown below:

Title page,
Item [74], *Attorney, Agent, or Firm*, reads "Braniga" should read -- Branigan --.

Column 8,
Line 6, "At" should read -- $\Delta t$ --.
Line 6, "$\tau$" should read -- $\tau 1$ --.
Line 17, "Ri" should read -- $\tau 1$ --.

Signed and Sealed this

Seventeenth Day of January, 2006

JON W. DUDAS
*Director of the United States Patent and Trademark Office*